United States Patent
Furukawa (10) Patent No.: US 9,261,483 B2
(45) Date of Patent: Feb. 16, 2016

(54) ACOUSTIC WAVE DETECTOR AND ACOUSTIC WAVE MEASUREMENT APPARATUS

(75) Inventor: Yukio Furukawa, Sagamihara (JP)

(73) Assignee: CANON KABUSHIKI KAISHA, Tokyo (JP)

(*) Notice: Subject to any disclaimer, the term of this patent is extended or adjusted under 35 U.S.C. 154(b) by 450 days.

(21) Appl. No.: 13/810,400

(22) PCT Filed: Jul. 8, 2011

(86) PCT No.: PCT/JP2011/003923
§ 371 (c)(1),
(2), (4) Date: Jan. 15, 2013

(87) PCT Pub. No.: WO2012/011243
PCT Pub. Date: Jan. 26, 2012

(65) Prior Publication Data
US 2013/0112001 A1 May 9, 2013

(30) Foreign Application Priority Data

Jul. 22, 2010 (JP) ................................. 2010-164553
Jun. 29, 2011 (JP) ................................. 2011-143868

(51) Int. Cl.
*G01N 29/00* (2006.01)
*A61B 5/00* (2006.01)
*A61B 8/08* (2006.01)
*A61B 8/13* (2006.01)
*G01N 21/17* (2006.01)

(52) U.S. Cl.
CPC .............. *G01N 29/00* (2013.01); *A61B 5/0095* (2013.01); *A61B 8/08* (2013.01); *A61B 8/13* (2013.01); *G01N 21/1702* (2013.01); *G01N 2021/1787* (2013.01)

(58) Field of Classification Search
CPC . A61B 5/0095; G01N 21/1702; G01N 29/00; G01F 1/661
USPC .............................. 73/655; 359/558, 566, 572
See application file for complete search history.

(56) References Cited

U.S. PATENT DOCUMENTS

| 2010/0053618 | A1 | 3/2010 | Nakajima et al. ............. 356/432 |
| 2012/0179022 | A1* | 7/2012 | Ichihara et al. ............... 600/407 |
| 2013/0231549 | A1 | 9/2013 | Yamamoto et al. ........... 600/407 |

FOREIGN PATENT DOCUMENTS

| JP | 60-235600 | 11/1985 |
| JP | 7-322393 | 12/1995 |
| WO | WO 2010/005109 | 1/2010 |

OTHER PUBLICATIONS

M. Xu et al., "Photoacoustic Imaging in Biomedicine", *Review of Scientific Instruments* 77, 041101 (Apr. 17, 2006).

J.J. Niederhauser et al., "Combined Ultrasound and Optoacoustic System for Real-Time High-Contrast Vascular Imaging in Vivo", *IEEE Transactions on Medical Imaging*, vol. 24, No. 4, pp. 436-440 (Apr. 2005).

Office Action issued on Jun. 30, 2015, in counterpart Japanese patent application 2011-143868, with English summary (above).

* cited by examiner

*Primary Examiner* — Hezron E Williams
*Assistant Examiner* — David Z Huang
(74) *Attorney, Agent, or Firm* — Fitzpatrick, Cella, Harper & Scinto (57) ABSTRACT

An acoustic wave detector includes: a transducer; and a light reflecting member which is positioned between the transducer and a subject surface that is irradiated with the light, and which reflects scattered light on the subject surface. The light reflecting member includes a first reflecting surface and a second reflecting surface positioned closer to the transducer than the first reflecting surface, and a distance between the first reflecting surface and the second reflecting surface is an odd multiple of a half wavelength of a predetermined wavelength included in an acoustic wave generated from the light reflecting member by the scattered light.

16 Claims, 8 Drawing Sheets

ACOUSTIC WAVE DETECTOR AND ACOUSTIC WAVE MEASUREMENT APPARATUS

TECHNICAL FIELD

The present invention relates to an acoustic wave detector and an acoustic wave measurement apparatus, and more particularly to an acoustic wave detector and an acoustic wave measurement apparatus employing a photoacoustic effect.

BACKGROUND ART

Photoacoustic tomography (PAT) for determining an optical property distribution of a subject such as a tissue with a high resolution by making use of a characteristic of an acoustic wave whereby less scattering occurs in the subject than with light has been proposed in recent years (see NPL1). When the tissue is irradiated with pulsed light from a light source, the light propagates while diffusing through the tissue. A light absorber contained in the tissue absorbs energy from the propagating pulsed light, and as a result, an acoustic wave (typically an ultrasonic wave) is generated (this phenomenon may be referred to as a photoacoustic effect). When the acoustic wave is detected (received) by an acoustic wave detector such as an ultrasonic probe, an acoustic wave signal serving as an electric signal is obtained. By analyzing the acoustic wave signal, an optical property distribution in the tissue, and in particular an optical energy absorption density distribution, can be obtained.

According to NPL1, a sound pressure (P) of an ultrasonic wave obtained from a light absorber in a tissue in PAT can be expressed by the following equation.

$$P = \Gamma \cdot \mu a \cdot \Phi \quad \text{[Math. 1]}$$

$\Gamma$ is a Grüneisen coefficient serving as an elasticity property, which is obtained by dividing the product of the square of a coefficient of cubic expansion ($\beta$) and acoustic velocity (c) by a specific heat (Cp) ($\Gamma = \beta c^2 / Cp$).

$\mu a$ is an absorption coefficient of the light absorber.

$\Phi$ is a local fluence (an amount of light entering the light absorber) in a local region.

The sound pressure of the acoustic wave obtained during PAT is commensurate with the local fluence reaching the light absorber. The light entering the tissue attenuates rapidly within the tissue due to scattering and absorption, and therefore the sound pressure of the acoustic wave generated in deep tissue in the tissue attenuates greatly in accordance with a distance from a light irradiation site.

A backward detection method in which the acoustic wave is detected by emitting light from the same side as the detector and a forward detection method in which the acoustic wave is detected by emitting light from the opposite side to the detector are known as acoustic wave detection methods. In backward detection type PAT, a method in which light is emitted diagonally from a flank of an acoustic wave detector so that the light is emitted effectively onto the back of the acoustic wave detector has been proposed (see NPL2). A main object of this literature is to irradiate a specific site of a tissue with light by disposing a mirror or a lens on the flank of the acoustic wave detector.

When backscattered light on the surface of the tissue enters the ultrasonic wave detector in backward detection type PAT, an ultrasonic wave generated by this light on a surface of the ultrasonic wave detector causes noise. To suppress this noise, a metal film (an aluminum coated plastic film) for reflecting scattered light is provided in front of the acoustic wave detector in NPL2.

Further, PTL1 discloses an example of an ultrasonic probe used in an ultrasonic diagnosis apparatus for obtaining an ultrasonic echo image, in which a metal having surface irregularities is provided on a front surface of the ultrasonic probe as an impedance matching layer. In this example, an average thickness of the impedance matching layer is preferably set at ¼ of a wavelength of the ultrasonic wave and a thickness of the irregularities is preferably set at +⅛, −⅛ of the wavelength of the ultrasonic wave. Note, however, that the metal layer is provided with the aim of widening a bandwidth of the ultrasonic probe and not reflecting scattered light.

CITATION LIST

Non Patent Literature

[NPL1] M. Xu, L. V. Wang, "Photoacoustic imaging in biomedicine", Review of scientific instruments, 77, 041101 (2006)

[NPL2] J. J. Niederhauser, M. Jaeger, R. Lemor, P. Weber and M. Frenz, IEEE Transactions on medical imaging, vol. 24, No. 4, 436 (2005)

Patent Literature

[PTL1] Japanese Patent Application Laid-Open No. H7-322393

SUMMARY OF INVENTION

As described above, when backscattered light on the surface of the tissue enters the acoustic wave detector, noise is generated, and an effective method of suppressing this noise is to provide a metal film, as described in NPL2.

However, the light cannot be reflected completely by the metal film, and a part of the energy of the light is absorbed by the metal film. Hence, an acoustic wave is inevitably generated from the metal film by the absorbed light. The acoustic wave generated from the metal film also produces noise, and this noise may lead to a reduction in the measurement quality of the PAT.

It is therefore an object of the present invention to provide a technique for suppressing noise caused by scattered light on a subject surface to a maximum extent in backward detection type PAT. Another object of the present invention is to provide a technique for suppressing noise generated from a light reflecting member for reflecting the scattered light on the subject surface to a maximum extent in backward detection type PAT.

The present invention in its first aspect provides an acoustic wave detector for detecting an acoustic wave generated by light emitted onto a subject, including: a transducer; and a light reflecting member which is positioned between the transducer and a subject surface that is irradiated with the light, and which reflects scattered light on the subject surface, wherein the light reflecting member includes a first reflecting surface and a second reflecting surface positioned closer to the transducer than the first reflecting surface, and a distance between the first reflecting surface and the second reflecting surface is an odd multiple of a half wavelength of a predetermined wavelength included in an acoustic wave generated from the light reflecting member by the scattered light.

The present invention in its second aspect provides an acoustic wave detector for detecting an acoustic wave generated by light emitted onto a subject, including: a transducer; and a light reflecting member which is positioned between the transducer and a subject surface that is irradiated with the light, and which reflects scattered light on the subject surface, wherein the light reflecting member is constituted by a metal layer having a sine wave-shaped cross-section, and an amplitude of the sine wave is an odd multiple of a half wavelength of a predetermined wavelength included in an acoustic wave generated from the light reflecting member by the scattered light.

The present invention in its third aspect provides an acoustic wave measurement apparatus including: the acoustic wave detector according to the first or second aspect; and a signal processing device for obtaining information relating to an interior of the subject from the acoustic wave detected by the acoustic wave detector.

According to the present invention, noise caused by scattered light on a subject surface (more specifically, noise generated from a light reflecting member for reflecting the scattered light on the subject surface) can be suppressed to a maximum extent during backward detection type PAT, and as a result, an improvement can be achieved in the quality of the PAT.

Further features of the present invention will become apparent from the following description of exemplary embodiments with reference to the attached drawings.

DESCRIPTION OF EMBODIMENTS

Best Mode for Carrying Out the Invention

The present invention relates to an acoustic wave detector that detects an acoustic wave (typically an ultrasonic wave) generated by light emitted onto a subject such as a tissue. The present invention also relates to an acoustic wave measurement apparatus including this type of acoustic wave detector and a signal processing device for obtaining information relating to an interior of the subject from the acoustic wave detected by the acoustic wave detector. A technique or an apparatus that obtains subject information using a photoacoustic effect in this manner is referred to as photoacoustic tomography (PAT). PAT may be used effectively to diagnose malignant tumors, blood vessel disorders, and the like, to observe the progress of chemotherapy, and so on. Note that the subject information indicates a generation source distribution of an acoustic wave generated by emitted light, for example an initial sound pressure distribution in a subject such as a tissue, an optical energy absorption density distribution derived therefrom, a concentration distribution of substances constituting a tissue obtained from this information, and so on. The substance concentration distribution is an oxygen saturation or the like, for example.

As described above, when backscattered light on a subject surface enters an acoustic wave detector during backward detection type PAT in which light is emitted from the same side as the acoustic wave detector, an acoustic wave generated by the light on the surface of the acoustic wave detector causes noise. Therefore, a light reflecting member is disposed between a (detection surface of) a transducer of the acoustic wave detector and the subject surface that is irradiated with the light. The light reflecting member reflects the scattered light on the subject surface, thereby preventing the scattered light from entering the transducer.

Further, in the present invention, a light reflecting member having a structure to be described below is used to suppress an acoustic wave generated from the light reflecting member itself. More specifically, the acoustic wave generated from the light reflecting member is an acoustic wave that is generated from the light reflecting member by the scattered light on the subject surface. In an embodiment of the present invention, the light reflecting member has a first reflecting surface and a second reflecting surface positioned closer to the transducer than the first reflecting surface. The light reflecting member preferably has N parallel (or substantially parallel) reflecting surfaces including the first reflecting surface and the second reflecting surface, where N is an integer of two or more. A distance between the first reflecting surface and the second reflecting surface is an odd multiple of a half wavelength of a predetermined wavelength included in the acoustic wave generated from the light reflecting member by the scattered light. The reflecting surfaces are preferably disposed to be parallel to the detection surface of the transducer of the acoustic wave detector. The aforesaid "predetermined wavelength" is preferably set at a wavelength, within a detection bandwidth of the transducer, at which noise suppression is most desirable. For example, the wavelength of a main component of the acoustic wave generated from the light reflecting member by the scattered light may be selected as the "predetermined wavelength". Alternatively, a subject wavelength to be detected by the acoustic wave detector, or more specifically a center wavelength of the detection bandwidth (sensitivity) of the transducer, a specific wavelength of an acoustic wave generated in a detection subject substance or a tissue, and so on may be selected as the "predetermined wavelength".

The light reflecting member may be constituted by a member in which first and second light reflecting films are formed respectively on either surface of a flat plate which is impedance-matched acoustically to the acoustic wave, for example. In this constitution, the first light reflecting film corresponds to the first reflecting surface and the second light reflecting film corresponds to the second reflecting surface. A thickness of the flat plate is preferably set to be equal to an odd multiple of half (a half wavelength) of the aforesaid predetermined wavelength. The flat plate which is impedance-matched acoustically to the acoustic wave (ultrasonic wave) is preferably made of a resin material, and polymethyl pentene is particularly favorable. A metal film made of gold (Au) or the like, a dielectric multilayer film designed in accordance with the wavelength of the emitted light, and so on may be used as the first and second light reflecting films.

Alternatively, the light reflecting member may be constituted by a metal layer formed with irregularities. In this constitution, a depressed portion (bottom surface) and a protruded portion (top surface) are formed parallel to each other so as to correspond to the first and second reflecting surfaces, respectively. A height difference between the depressed portion and the protruded portion is set to be equal to an odd multiple of half (a half wavelength) of the aforesaid predetermined wavelength. Further, irregularities having a staircase-shaped cross-section may be formed such that each step serves as a reflecting surface. When three or more reflecting surfaces are formed, an interval between the reflecting surfaces is preferably set at an integer fraction of half (a half wavelength) of the aforesaid predetermined wavelength. Note that parts of the metal layer other than the reflecting surfaces (for example, a part connecting the reflecting surfaces to each other) are preferably formed to be perpendicular to the reflecting surface (in other words, perpendicular to the detection surface of the acoustic wave detector).

In another embodiment of the present invention, the light reflecting member may be constituted by a metal layer formed with a sine wave-shaped cross-section. In this constitution, an amplitude of the sine wave is set at an odd multiple of half (a half wavelength) of the aforesaid predetermined wavelength.

The manner in which the constitutions described above are able to suppress noise caused by an acoustic wave generated from the light reflecting member will be described below with reference to FIGS. 3A to 5B.

Figure 3A:
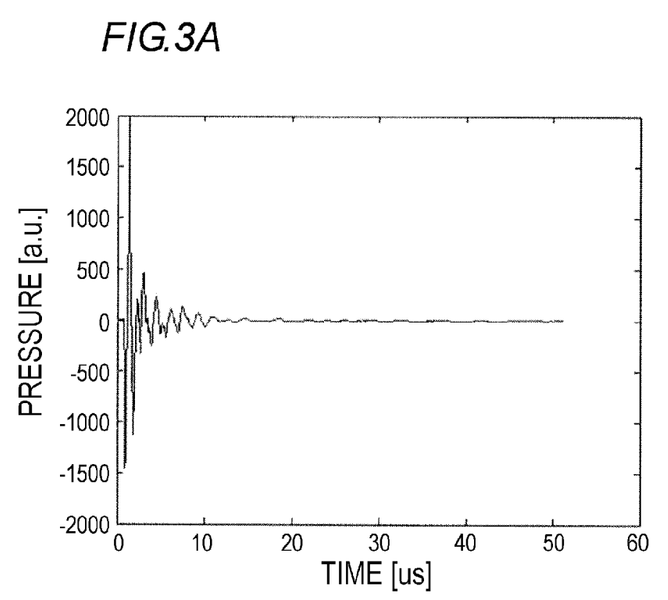
FIGS. 3A, 3B are views illustrating noise generated by a conventional light reflecting member.
Figure 3B:
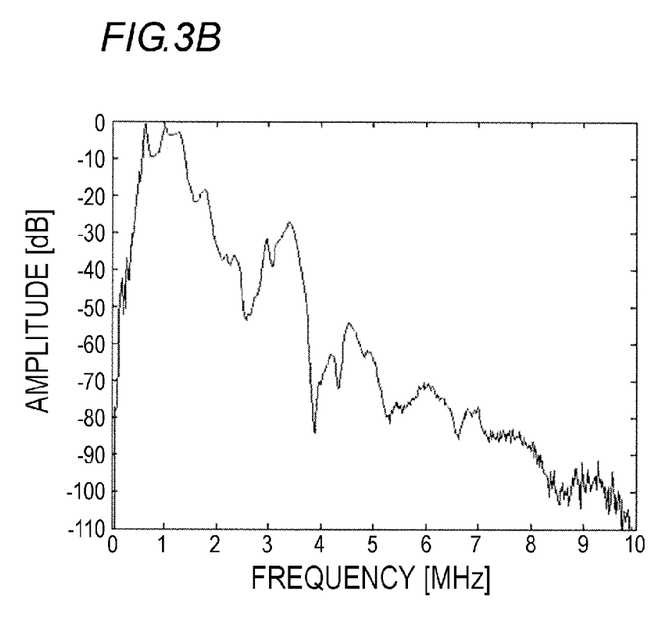

FIGS. 3A, 3B are views illustrating problems inherent in a conventional light reflecting member. FIGS. 3A, 3B show a waveform of an acoustic wave from a light reflecting member, which is detected by an acoustic wave detector in a case where a single flat metal film is used as the light reflecting member. In FIG. 3A, time is shown on the abscissa and the intensity of the acoustic wave is shown on the ordinate. In FIG. 3B, the abscissa is converted to a frequency axis.

Figure 4A:
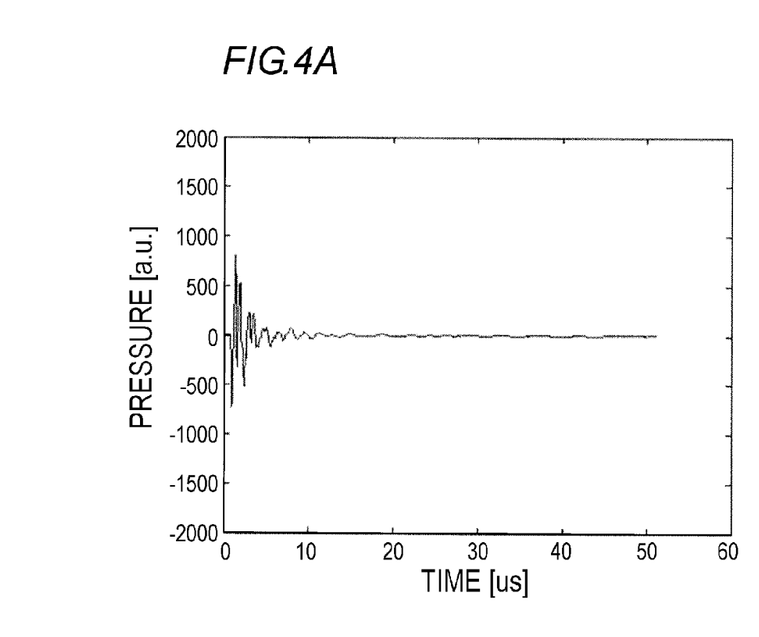
FIGS. 4A, 4B are views illustrating a manner in which noise generated by a light reflecting member according to an embodiment of the present invention is suppressed.
Figure 4B:
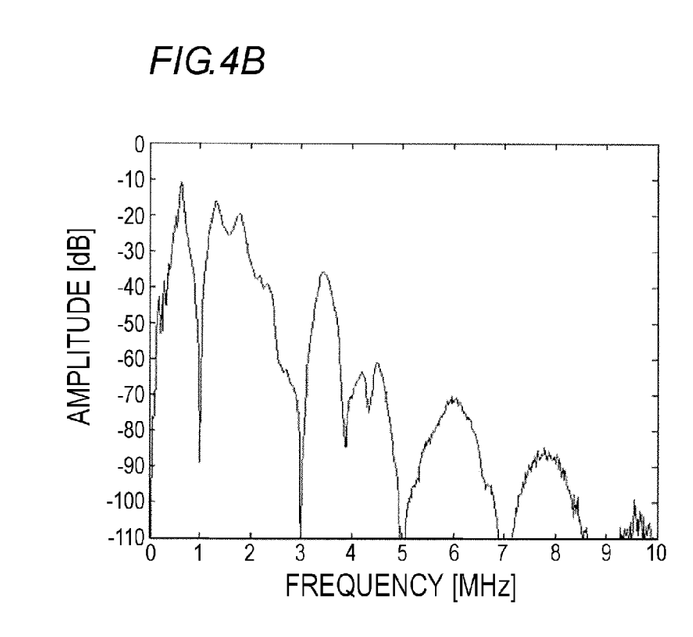

FIGS. 4A, 4B show waveforms of an acoustic wave detected by an acoustic wave detector in a case where the employed light reflecting member has two parallel reflecting surfaces and the interval between the reflecting surfaces is set to be equal to an odd multiple of half (a half wavelength) of the wavelength of an acoustic wave having a frequency of 1 MHz. The shapes and characteristics (reflectance and so on) of the respective reflecting surfaces are determined such that the intensity of the acoustic wave generated by the first reflecting surface is substantially equal to the intensity of the acoustic wave generated by the second reflecting surface. Specific examples of the shapes and characteristics of the reflecting surfaces will be described in following embodiments, and have therefore been omitted here.

It is evident by comparing FIGS. 3A to 4B that on the temporal axis, the amplitude of the acoustic wave decreases by approximately half, while on the frequency axis, the intensity of the acoustic wave can be attenuated at a frequency of 1 MHz. The reason for this is that with a 1 MHz acoustic wave, the acoustic wave generated by the first reflecting surface and the acoustic wave generated by the second reflecting surface reach the acoustic wave detector at an offset of a half wavelength or an odd multiple of the half wavelength, and therefore the 1 MHz component is attenuated.

Figure 5A:
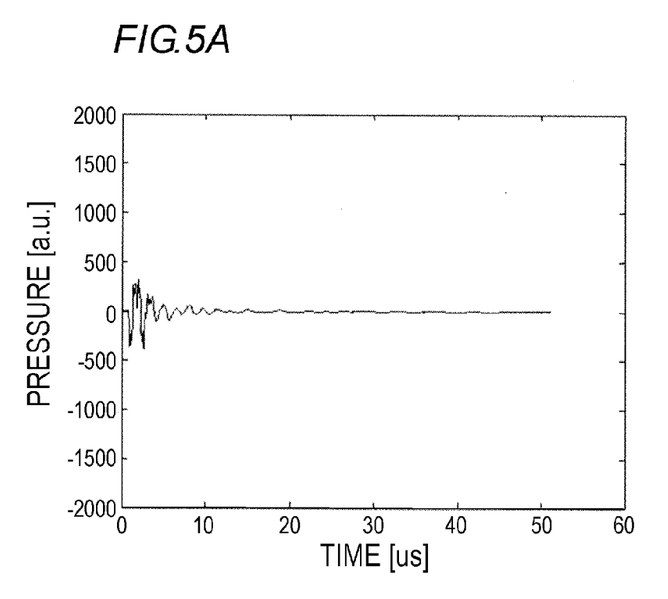
FIGS. 5A, 5B are views illustrating a manner in which noise generated by the light reflecting member according to this embodiment of the present invention is suppressed.
Figure 5B:
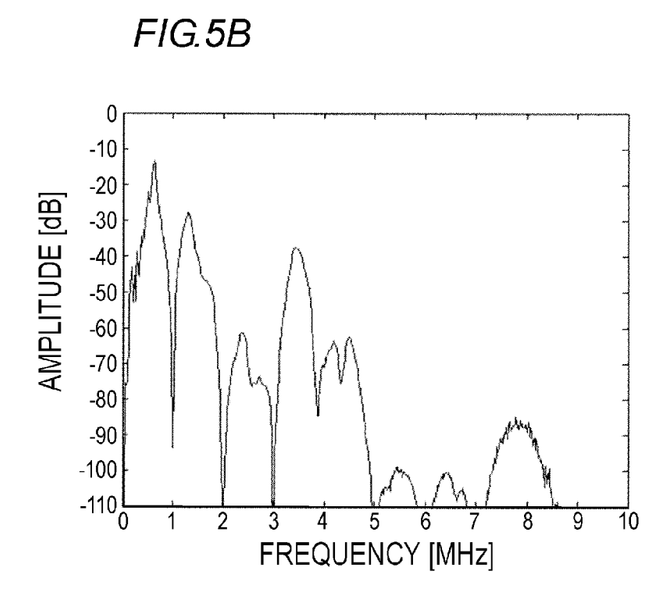

FIGS. 5A, 5B show waveforms of an acoustic wave detected by the acoustic wave detector in a case where the employed light reflecting member has four parallel reflecting surfaces and the intervals between the reflecting surfaces are set to be equal to a quarter of the wavelength of a 1 MHz acoustic wave. It is evident by comparing FIGS. 3A to 4B that, in addition to a 1 MHz acoustic wave, a 2 MHz can also be attenuated.

Hence, according to the embodiment described above, an acoustic wave from a light reflecting member that produces noise in a signal from a subject can be suppressed. The frequency of the acoustic wave to be suppressed may be determined in accordance with the frequency of the acoustic wave generated from the subject and the frequency bandwidth of the transducer, for example.

Specific embodiments will be described below.

First Embodiment

Figure 1:
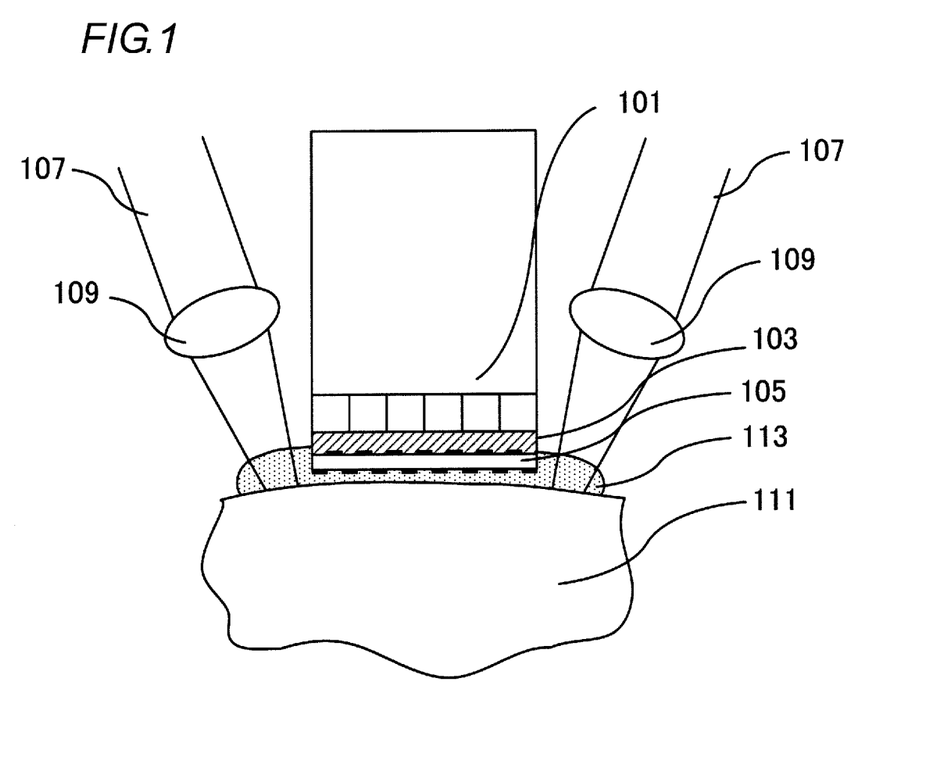
FIG. 1 is a view illustrating a first embodiment.

FIG. 1 is a schematic diagram showing the main parts of an acoustic wave measurement apparatus according to a first embodiment of the present invention. In FIG. 1, 101 is an acoustic wave detector. The acoustic wave detector 101 includes a plurality of transducers disposed in an array over a detection surface, and a center wavelength of a detection bandwidth thereof is set at 1 MHz. 103 is a resin impedance matching layer formed on a front surface of the acoustic wave detector 101 for acoustic impedance matching, and 105 is a light reflecting member. 107 denotes pulsed light emitted from a laser light source, not shown in the drawing, and 109 is a lens. 111 is a tissue serving as a subject, and 113 is an optically transmissive gel that effectively guides an acoustic wave generated in the tissue to the acoustic wave detector 101. Although not shown in the drawing, the acoustic wave measurement apparatus also includes a laser light source for emitting the pulsed light, a circuit for performing AD conversion on an electric signal (an acoustic wave signal) output by the acoustic wave detector 101, a signal processing device (a computer) for analyzing a digital acoustic wave signal, and so on.

The pulsed light 107 is emitted onto the tissue via the lens 109 and the gel 113. A light absorber contained in tissue of the tissue 111 absorbs the energy of the propagating pulsed light 107 such that an acoustic wave is generated. The acoustic wave generated in the tissue passes through the gel 113, the light reflecting member 105, and the impedance matching layer 103 so as to be detected by the transducers of the acoustic wave detector 101. By analyzing the detected acoustic wave signal, an optical property distribution of the tissue 111, and in particular an optical energy absorption density distribution, can be obtained. A typical known method may be used to analyze the acoustic wave signal.

Figure 2A:
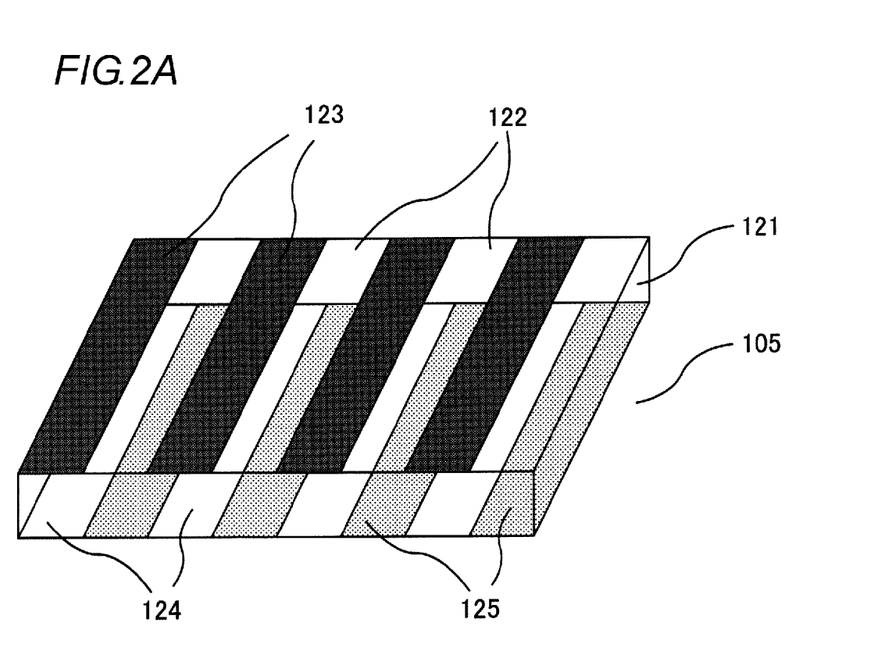
FIGS. 2A, 2B are views illustrating a light reflecting member according to the first embodiment.
Figure 2B:
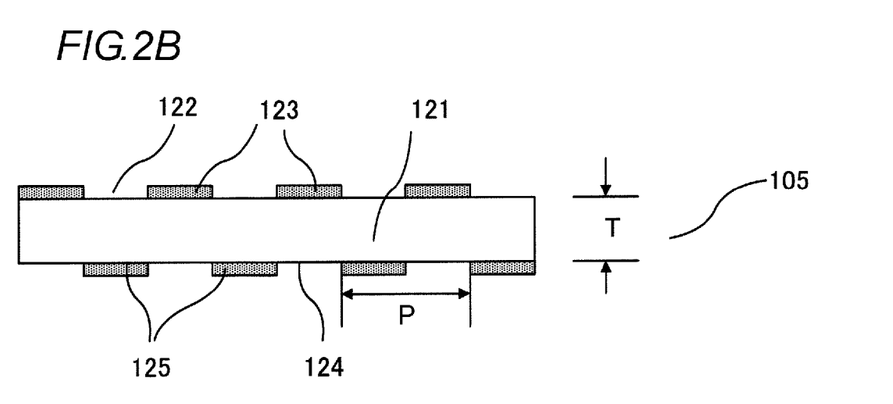

Using FIGS. 2A, 2B, the constitution of the light reflecting member 105 will be described.

The light reflecting member 105 is constituted by a polymethyl pentene flat plate 121 having a thickness T that is half a wavelength of an acoustic wave having a frequency of 1 MHz, and a plurality of light reflecting films 123, 125 made of Au and provided on either surface of the flat plate 121. More specifically, the light reflecting film 125 serving as a reflection region for reflecting light and a window 124 serving as an open region for transmitting light are arranged alternately on a tissue side surface (a first reflecting surface) of the light reflecting member 105. Similarly, the light reflecting film 123 serving as a reflection region and a window 122 serving as an open region are arranged alternately on a transducer side surface (a second reflecting surface) of the light reflecting member 105.

In this embodiment, the light reflecting films 123, 125 are disposed on the respective reflecting surfaces alternately such that when the light reflecting film 125 on one reflecting surface is projected onto the other reflecting surface, a projected image of the light reflecting film 125 does not overlap the light reflecting film 123. Further, the light reflecting films 123, 125 on the respective reflecting surfaces are set to have a substantially identical surface area. With this constitution, when scattered light enters from the tissue side of the light reflecting member 105, an amount of light emitted onto the light reflecting film 125 is substantially equal to an amount of light emitted onto the light reflecting film 123 through the window 124 and the flat plate 121. Note that light absorption by the flat plate 121 is small enough to be ignored. As a result, amplitudes of the acoustic waves generated respectively from the light reflecting films 123, 125 are substantially equal. The thickness of the flat plate 121 is set at half the wavelength of a 1 MHz acoustic wave generated when the light reflecting films 123, 125 constituting the light reflecting member are irradiated with scattered light, and therefore the acoustic wave generated from the light reflecting member 105 and detected by the acoustic wave detector 101 is suppressed. In other words, the thickness of the flat plate 121 is set at half the wavelength of a 1 MHz acoustic wave serving as the main component of the acoustic wave generated when the light reflecting films are irradiated with scattered light, and therefore the acoustic wave generated from the light reflecting member 105 and detected by the acoustic wave detector 101 is suppressed.

Further, a pitch P of the windows 122, 124 provided in the light reflecting films 123, 125 is set at a length corresponding to the wavelength of an acoustic wave having a frequency of 1 MHz. In this case, the 1 MHz component of the acoustic wave generated by the light reflecting member 105 intensifies along an arrangement direction of the windows 122, 124 so as to propagate more easily in that direction. This means that an acoustic wave of this component is less likely to reach the acoustic wave detector 101. In other words, the 1 MHz component of the acoustic wave generated by the light reflecting member 105 is unlikely to be detected by the acoustic wave detector 101.

Meanwhile, the acoustic wave from the tissue 111 attenuates slightly while passing through the light reflecting member 105. However, attenuation is caused by the flat plate 121 and either one of the light reflecting films in all locations of the light reflecting member 105, and therefore the attenuation occurs substantially evenly. Therefore, image deterioration caused by the light reflecting member 105 during analysis of the detected acoustic wave signal from the tissue 111 is small.

With the constitution described above, an acoustic wave from the light reflecting member 105 that produces noise can be suppressed effectively, and therefore an SN ratio of the biological information (for example, an image representing the optical property distribution of the tissue interior) can be improved.

In this embodiment, dielectric multilayer films may be used as the light reflecting films 123, 125. Further, the material of the flat plate 121 is not limited to polymethyl pentene. Furthermore, here, gel is used as an interface with the tissue, but the present invention is not limited thereto, and water, oil, or another material, for example, may be used instead. Moreover, a solid state laser such as a YAG laser or a titanium-sapphire laser or a semiconductor laser may be used as the laser light source.

Second Embodiment

Figure 6A:
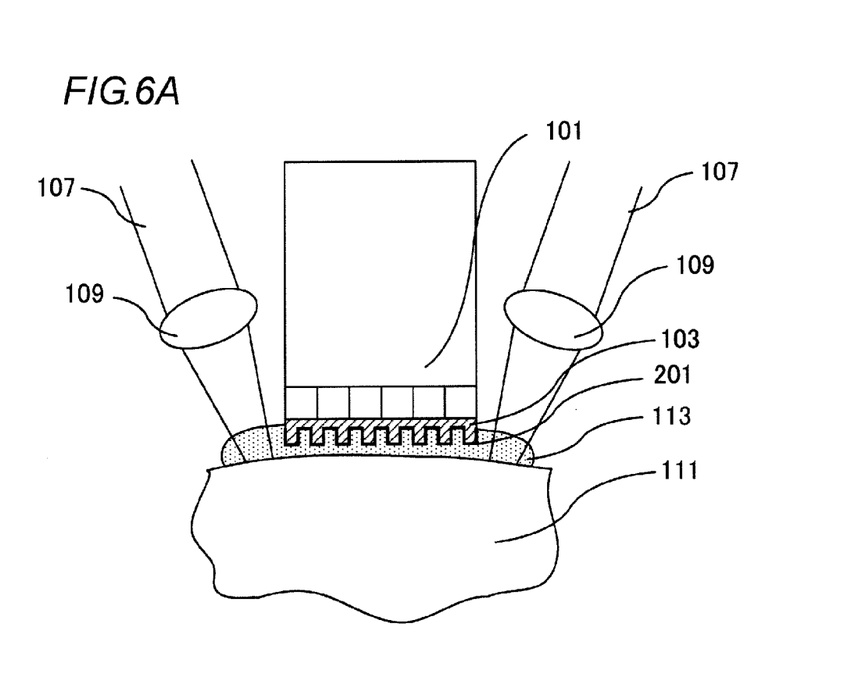
FIGS. 6A, 6B are views illustrating a light reflecting member according to a second embodiment.

FIG. 6A is a schematic diagram illustrating a second embodiment of the present invention. Identical members to those in FIG. 1 have been allocated identical reference numerals, and description thereof has been omitted. The second embodiment differs from the first embodiment in that a light reflecting member 201 is constituted by a metal layer formed with a depressed portion and a protruded portion, and a height difference between the depressed portion and the protruded portion is set at half the wavelength of a 1 MHz acoustic wave generated from the metal film when the metal film is irradiated with scattered light from the subject.

Figure 6B:
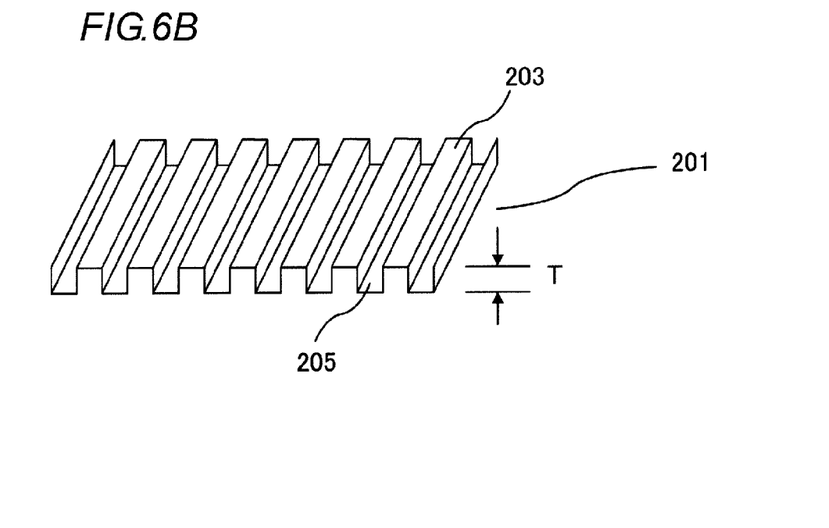

FIG. 6B is a view illustrating the light reflecting member 201. The light reflecting member 201 includes a first light reflecting surface 203 constituted by a protruded portion (a top surface) and a second light reflecting surface 205 constituted by a depressed portion (a bottom surface). The light reflecting surface 203 and the light reflecting surface 205 have substantially equal surface areas, and therefore the respective light reflecting surfaces are irradiated with substantially equal amounts of light. As a result, acoustic waves having substantially equal amplitudes are generated from the respective light reflecting surfaces. A height difference T between the depressed portion and the protruded portion is set at half the wavelength of a 1 MHz acoustic wave, and therefore the 1 MHz frequency component of an acoustic wave generated from the light reflecting member 201 and detected by the acoustic wave detector 101 is suppressed. Hence, the acoustic wave from the light reflecting member 201 that produces noise can be suppressed effectively, and as a result, the SN ratio of the image can be improved.

In this embodiment, there are no particular limitations on the pitch of the depressed portion and protruded portion, but the pitch may be set at a length corresponding to the wavelength of an acoustic wave having a frequency of 1 MHz, as in the first embodiment.

Third Embodiment

Figure 7:
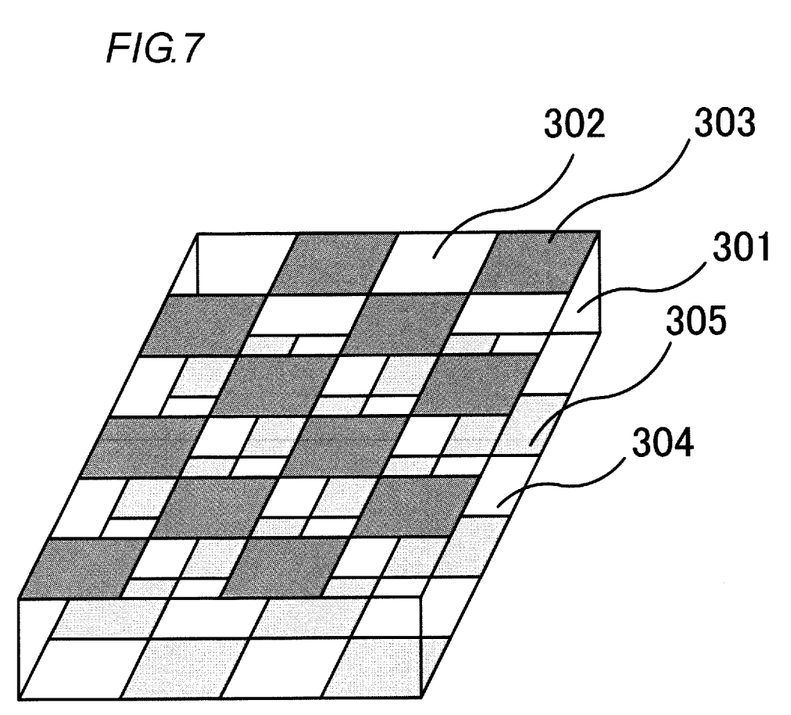
FIG. 7 is a view illustrating a light reflecting member according to a third embodiment.

FIG. 7 is a schematic diagram illustrating a light reflecting member according to a third embodiment of the present invention. In this embodiment, the light reflecting member is constituted by a flat plate 301 and light reflecting films (reflection regions) 303, 305 made of Au and provided on either side of the flat plate 301. This embodiment differs from the first embodiment in that in the first embodiment, the windows (122, 124) are disposed periodically in a single direction over the reflecting surfaces, whereas in this embodiment, windows 302, 304 are disposed periodically in two directions (two dimensionally) over the reflecting surfaces. Likewise in this embodiment, the light reflecting films 303, 305 on the respective reflecting surfaces are disposed alternately so as not to overlap when projected onto a single reflecting surface.

In this embodiment, the pitch of the windows 302, 304 is set at a predetermined length (for example, an identical length to the wavelength of the 1 MHz acoustic wave that is generated from the light reflecting member when the light reflecting member is irradiated with scattered light from the subject), and therefore the acoustic wave generated by the light reflecting member can propagate dominantly in two directions over the surfaces of the flat plate 301.

For example, when the acoustic wave detector includes transducers in a one-dimensional array, the acoustic wave may be propagated in a perpendicular direction to the arrangement direction of the transducers of the acoustic wave detector using a light reflecting member having a one-dimensional period structure, such as that of the first embodiment. When the acoustic wave detector includes transducers in a two-dimensional array, on the other hand, a light reflecting member having a two-dimensional period structure, such as that of this embodiment, may be used.

Fourth Embodiment

Figure 8:
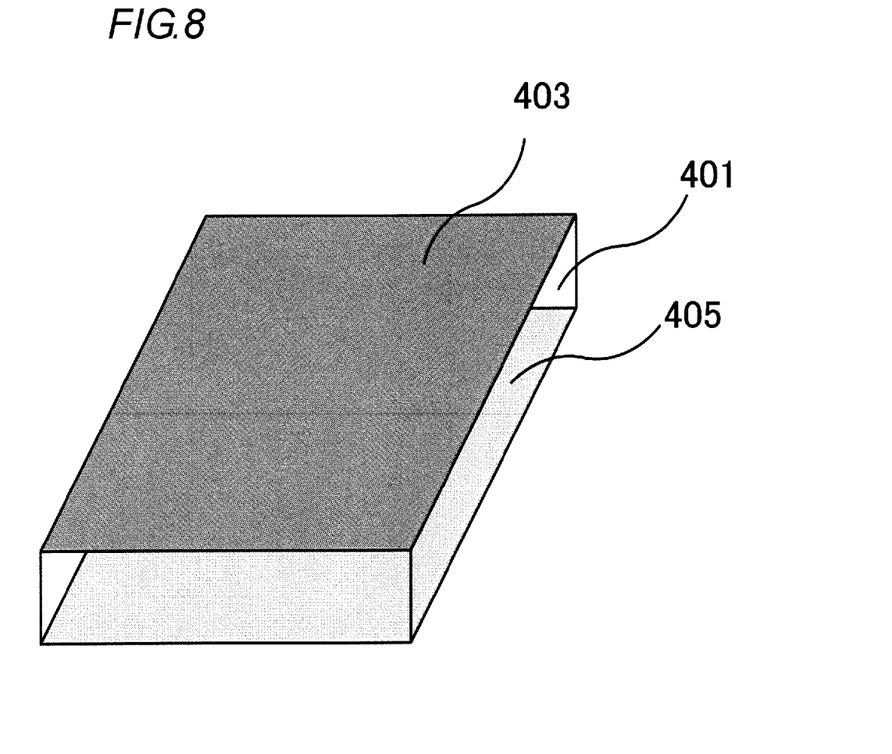
FIG. 8 is a view illustrating a light reflecting member according to a fourth embodiment.

FIG. 8 is a schematic diagram illustrating a light reflecting member according to a fourth embodiment of the present invention. In this embodiment, the light reflecting member is constituted by a flat plate 401 and light reflecting films 403, 405 provided on either side thereof. The light reflecting films 403, 405 are constituted by Au layers having a different thickness, wherein the light reflecting film 403 is adjusted to a film thickness at which an optical reflectance of at least 0.8 is obtained and the light reflecting film 405 is adjusted to a film thickness at which an optical reflectance between 0.4 and 0.5 is obtained. Further, the light reflecting member is disposed such that the light reflecting film 403 having the greater light reflectance is positioned on the transducer side and the light reflecting film 405 having the smaller light reflectance is positioned on the tissue side.

In this embodiment, backscattered light from the tissue is emitted onto the light reflecting film 405 first. Part of the light is reflected, another part is transmitted, and a small light component is absorbed such that an acoustic wave is generated. The light that passes through the light reflecting film 405 enters the light reflecting film 403, where a small light component is likewise absorbed such that an acoustic wave is generated. According to the optical reflectance relationship, amounts of light entering the light reflecting films 403, 405 are substantially equal, and the amplitudes of the generated acoustic waves are also substantially equal. Hence, by setting the thickness of the flat plate 401 at half the wavelength of the acoustic wave generated by the light reflecting films, the acoustic wave from the light reflecting member that produces noise can be suppressed effectively, similarly to the embodiments described heretofore, and as a result, the SN ratio of the image can be improved.

Fifth Embodiment

Figure 9:
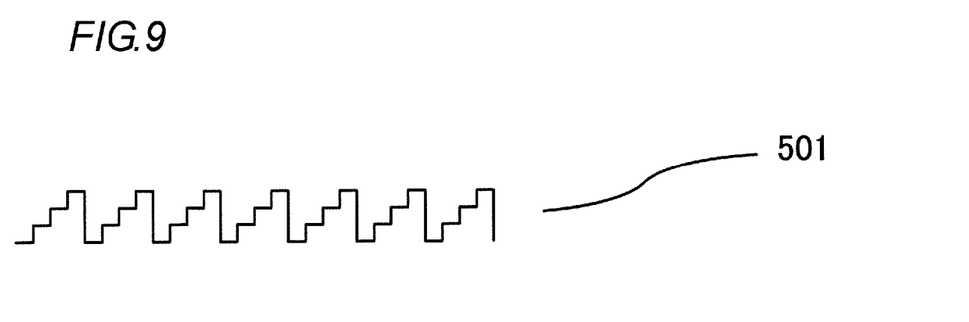
FIG. 9 is a view illustrating a light reflecting member according to a fifth embodiment.

FIG. 9 is a schematic diagram illustrating a light reflecting member according to a fifth embodiment of the present invention. In the second embodiment, an example of a light reflecting member formed from a metal layer having two surfaces constituted by a depressed portion and a protruded portion was described. In this embodiment, on the other hand, a light reflecting member 501 is formed from a metal layer having reflecting surfaces with a four step structure. In this embodiment, an interval between the reflecting surfaces is set at a quarter of the wavelength of an acoustic wave having the most undesirable frequency. Therefore, for example, when the most undesirable frequency is 1 MHz, a 2 MHz component of the acoustic wave generated from the light reflecting member 501 can be suppressed in addition to the 1 MHz component.

In this embodiment, a four step structure was described as an example, but this embodiment is not limited thereto and may also be applied to a light reflecting member in which light reflecting films are provided on either side of a flat plate, as in the first embodiment. In this case, three flat plates may be laminated together, and light reflecting films provided with appropriate windows may be disposed between the flat plates and on the surfaces on either side.

OTHER EMBODIMENTS

In the first to third embodiments, examples of light reflecting members having period structures in one or two directions were described, but the present invention is not limited thereto, and a concentric period structure may be employed. More specifically, reflection regions and open regions may be disposed alternately in radial form about a certain point on the reflecting surface. In this case also, a pitch of the open regions is preferably equal to the aforesaid predetermined wavelength. Further, similar effects to those described above can be obtained by forming the light reflecting member from a metal layer having a sine wave-shaped cross-section and setting the amplitude thereof at a length corresponding to half the aforesaid predetermined wavelength. In this case also, the pitch of the sine wave is preferably equal to the aforesaid predetermined wavelength.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-164553, filed on Jul. 22, 2010 and Japanese Patent Application No. 2011-143868, filed on Jun. 29, 2011, which are hereby incorporated by reference herein in their entirety.

The invention claimed is:

1. An acoustic wave detector for detecting an acoustic wave generated by light emitted onto a subject, comprising:
   a transducer; and
   a light reflecting member which is positioned between said transducer and a subject surface that is irradiated with the light, and which reflects scattered light on the subject surface, wherein
   said light reflecting member includes a first reflecting surface and a second reflecting surface positioned closer to said transducer than said first reflecting surface, and
   said first reflecting surface and said second reflecting surface are disposed such that a distance between said first reflecting surface and said second reflecting surface is a predetermined length equal to an odd multiple of a half wavelength of a predetermined wavelength, said predetermined wavelength being within a detection bandwidth of said transducer and included in an acoustic wave generated from said light reflecting member by the scattered light.

2. The acoustic wave detector according to claim 1, wherein said first reflecting surface and said second reflecting surface respectively include a reflection region that reflects light and an open region that transmits light, and
   a projected image obtained when said reflection region of said first reflecting surface is projected onto said second reflecting surface does not overlap said reflection region of said second reflecting surface.

3. The acoustic wave detector according to claim 2, wherein said first reflecting surface or said second reflecting surface includes a plurality of open regions,
   said plurality of open regions on said first reflecting surface or said plurality of open regions on said second reflecting surface are disposed in a predetermined pitch over said first reflecting surface or said second reflecting surface, respectively, and
   said predetermined pitch is equal to the predetermined wavelength.

4. The acoustic wave detector according to claim 1, wherein an optical reflectance of said first reflecting surface is smaller than an optical reflectance of said second reflecting surface.

5. The acoustic wave detector according to claim 4, wherein said light reflecting member is a member having a flat plate and first and second light reflecting films, in which said first and second light reflecting films correspond respectively to said first and second light reflecting surfaces and are formed on either surface of said flat plate, which is impedance-matched acoustically to the acoustic wave, and a thickness of said flat plate is an odd multiple of a half wavelength of the predetermined wavelength.

6. The acoustic wave detector according to claim 1, wherein said light reflecting member is a member having a flat plate and first and second light reflecting films, in which said first and second light reflecting films corresponding respectively to said first and second light reflecting surfaces and are formed on either surface of said flat plate, which is impedance-matched acoustically to the acoustic wave, and
a thickness of said flat plate is an odd multiple of a half wavelength of the predetermined wavelength.

7. The acoustic wave detector according to claim 1, wherein said light reflecting member is a metal layer formed with a depressed portion and a protruded portion corresponding respectively to said first and second reflecting surfaces, and
a height difference between said depressed portion and said protruded portion is an odd multiple of a half wavelength of the predetermined wavelength.

8. The acoustic wave detector according to claim 1, wherein the predetermined wavelength is a center wavelength of a detection bandwidth of said transducer.

9. An acoustic wave measurement apparatus comprising:
an acoustic wave detector for detecting an acoustic wave generated by light emitted onto a subject; and
a signal processing device for obtaining information relating to an interior of the subject from the acoustic wave detected by said acoustic wave detector, wherein
said acoustic wave detector comprises:
a transducer; and
a light reflecting member which is positioned between said transducer and a subject surface that is irradiated with the light, and which reflects scattered light on the subject surface,
wherein said light reflecting member includes a first reflecting surface and a second reflecting surface positioned closer to said transducer than said first reflecting surface, and
wherein said first reflecting surface and said second reflecting surface are disposed such that a distance between said first reflecting surface and said second reflecting surface is a predetermined length equal to an odd multiple of a half wavelength of a predetermined wavelength, said predetermined wavelength being within a detection bandwidth of said transducer and included in an acoustic wave generated from said light reflecting member by the scattered light.

10. An acoustic wave detector for detecting an acoustic wave generated by light emitted onto a subject, comprising:
a transducer; and
a light reflecting member which is positioned between said transducer and a subject surface that is irradiated with the light, and which reflects scattered light on the subject surface,
wherein said light reflecting member includes a first reflecting surface and a second reflecting surface positioned closer to said transducer than said first reflecting surface, and an optical reflectance of said first reflecting surface is smaller than an optical reflectance of said second reflecting surface.

11. The acoustic wave detector according to claim 10, wherein said light reflecting member is a member having a flat plate and first and second light reflecting films, in which said first and second light reflecting films correspond respectively to said first and second light reflecting surfaces and are formed on either surface of said flat plate, which is impedance-matched acoustically to the acoustic wave.

12. The acoustic wave detector according to claim 10, wherein said light reflecting member is a metal layer formed with a depressed portion and a protruded portion corresponding respectively to said first and second reflecting surfaces.

13. An acoustic wave detector for detecting an acoustic wave generated by light emitted onto a subject, comprising:
a transducer; and
a light reflecting member which is positioned between said transducer and a subject surface that is irradiated with the light, and which reflects scattered light on the subject surface,
wherein said light reflecting member includes a first reflecting surface and a second reflecting surface positioned closer to said transducer than said first reflecting surface,
said first reflecting surface and said second reflecting surface respectively include a reflection region that reflects light and an open region that transmits light, and
a projected image obtained when said reflection region of said first reflecting surface is projected onto said second reflecting surface does not overlap said reflection region of said second reflecting surface.

14. The acoustic wave detector according to claim 13, wherein said light reflecting member is a member having a flat plate and first and second light reflecting films, in which said first and second light reflecting films correspond respectively to said first and second light reflecting surfaces and are formed on either surface of said flat plate, which is impedance-matched acoustically to the acoustic wave.

15. The acoustic wave detector according to claim 13, wherein said first reflecting surface or said second reflecting surface includes a plurality of open regions, and
said plurality of open regions on said first reflecting surface or said plurality of open regions on said second reflecting surface are disposed in a predetermined pitch over said first reflecting surface or said second reflecting surface, respectively.

16. The acoustic wave detector according to claim 13, wherein said light reflecting member is a metal layer formed with a depressed portion and a protruded portion corresponding respectively to said first and second reflecting surfaces.

* * * * *